(12) United States Patent
Mould

(10) Patent No.: US 6,179,770 B1
(45) Date of Patent: Jan. 30, 2001

(54) COIL ASSEMBLIES FOR MAGNETIC STIMULATORS

(75) Inventor: Stephen Mould, Whitland (GB)

(73) Assignee: Magstim Company Limited, Dyfed (GB)

( * ) Notice: Under 35 U.S.C. 154(b), the term of this patent shall be extended for 0 days.

(21) Appl. No.: 09/293,061

(22) Filed: Apr. 16, 1999

(30) Foreign Application Priority Data

Apr. 25, 1998 (GB) .................................................. 9808764

(51) Int. Cl.[7] .......................................................... A61N 1/00
(52) U.S. Cl. .................................................. 600/13; 600/15
(58) Field of Search ............................................ 600/9–15

(56) References Cited

U.S. PATENT DOCUMENTS

| | | | |
|---|---|---|---|
| 4,989,604 | * | 2/1991 | Fang .......................................... 607/2 |
| 5,061,234 | * | 10/1991 | Chaney ................................... 600/14 |
| 5,718,662 | * | 2/1998 | Jalinous ................................. 600/13 |
| 5,766,124 | * | 6/1998 | Polson .................................... 600/13 |
| 5,857,957 | * | 1/1999 | Lin ......................................... 600/13 |

* cited by examiner

Primary Examiner—John P. Lacyk
(74) Attorney, Agent, or Firm—Nixon & Vanderhye P.C.

(57) ABSTRACT

A magnetic stimulator for neuro-muscular tissue uses a stimulating coil and generates a succession of electrical discharge pulses from the coil to produce magnetic pulses which induce electrical signals in the tissue. The coil has at least one set of generally circular turns, and is disposed within a casing connected to a conduit through which extend cables for the supply of electrical power to the coil. The conduit and casing allow for the flow of gaseous coolant around and over exposed surfaces of the coil, though the casing and along the conduit.

9 Claims, 3 Drawing Sheets

COIL ASSEMBLIES FOR MAGNETIC STIMULATORS

FIELD OF THE INVENTION

This invention relates to coil assemblies for magnetic stimulators intended for the electro-magnetic stimulation of neuro-muscular tissue. The invention particularly relates to an improved construction which provides for the supply of electrical power and the flow of coolant by way of the same conduit.

BACKGROUND TO THE INVENTION

It is known, for example from British patent 2298370 to provide a rapidly changing magnetic field, of the order of 20 kiloteslas per second, in the vicinity of tissue in order to induce electric current in the tissue and thereby stimulate the tissue.

Known magnetic stimulators comprise generally a charging circuit, a capacitor, a discharge control such as a control rectifier, and a coil which is of a size and power rating appropriate for the generation of the very large magnetic fields which magnetic stimulators require. Typically, the coil may be of a size adapted to fit partly over the cranium of a human patient. Others forms of coil are, as exemplified herein, in the shape of a large figure of eight.

In the aforementioned patent and also in U.S. Pat. Nos. 5,718,662 and 5766124 there are described stimulators which are capable of providing a rapid sequence of discharge pulses through the stimulating coil. Such a rapid sequence of pulses is useful in, for example, transcranial magnetic stimulation.

However, owing to the very large energy contained in the pulses, such a stimulation technique is very liable to produce overheating of a stimulating coil. It is known to provide in a stimulating system of this general nature, some means of monitoring the temperature in the vicinity of a stimulating coil and to provide some inhibiting function, such as disabling the stimulating system if a coil should overheat. It is customary to change coils in those circumstances.

The present invention has the general object of avoiding the need to change coils unnecessarily and is based on a coil design which allows cooling by the flow of a coolant gas around substantially all the exposed surfaces of the stimulating coil and preferably also a supply cable to it.

Other features and advantages of the invention will be apparent from the accompanying drawings.

DESCRIPTION OF THE PREFERRED EMBODIMENT

Figure 1:
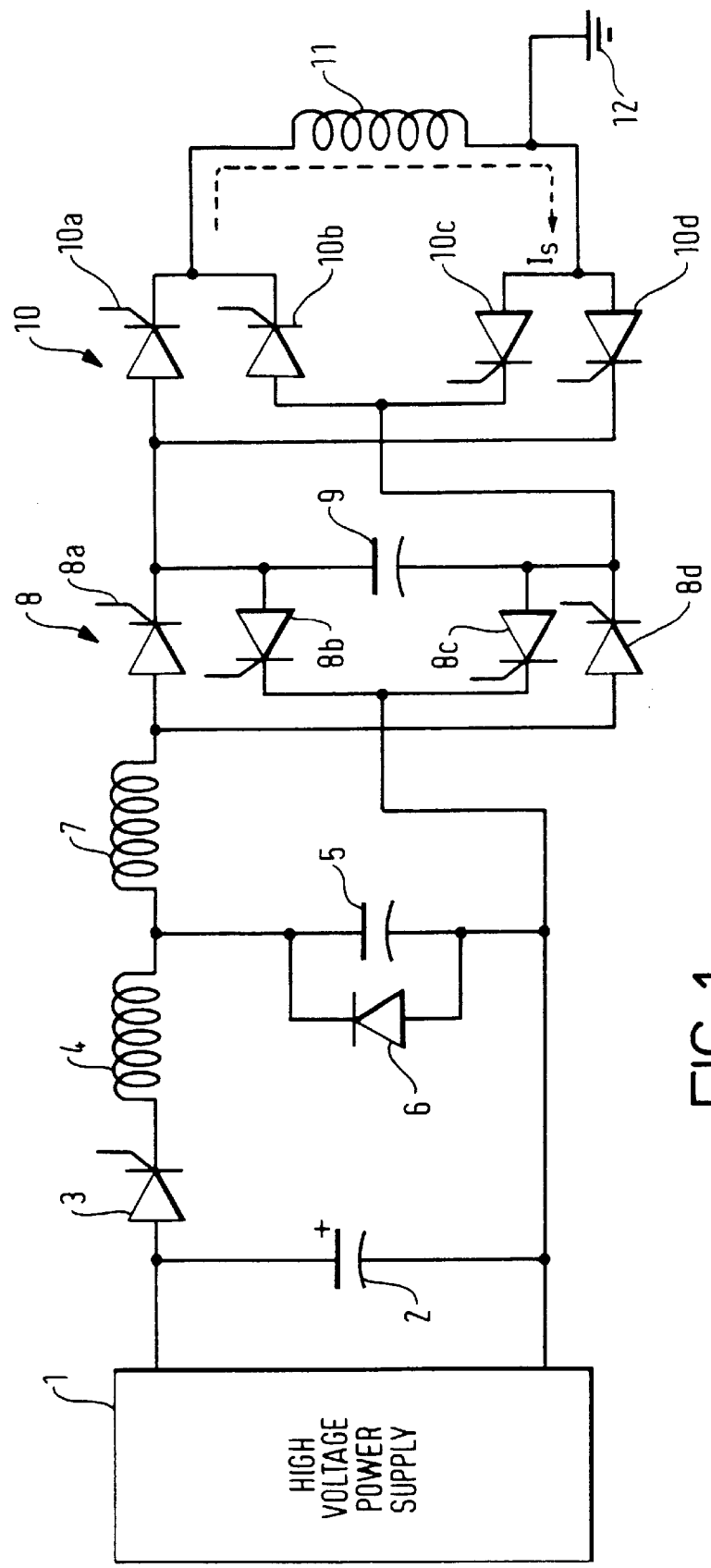
FIG. 1 is an illustration of a known circuit for providing high power pulses to a stimulating coil for neuro-muscular tissue stimulation.

FIG. 1 illustrates one channel of a stimulating system corresponding to that described in our British patent number 2298370.

A high voltage power supply 1 is provided for charging a reservoir capacitor 2. Discharge of the reservoir capacitor is controlled by a controllable series switch 3 which may be a controlled rectifier such as a thyristor. The switch 3 is connected to a series inductor 4, which is connected to the upper plate of a transfer capacitor 5 of which the lower plate is connected to the lower plate of capacitor 2. A reverse diode 6 is connected across the capacitor 5, the diode blocking current in the direction of normal current flow through the switch 3 and the inductor 4.

The upper plate of the transfer capacitor 5 is connected by way of an inductor 7 to the anodes of two thyristor switches 8a and 8d of which the cathodes are connected to opposite plates of a third, discharge, capacitor 9. The inductor 7, like inductor 4, is a current limiter which is capable of transient energy storage. The lower plate of the transfer capacitor 5 is connected to the cathodes of thyristors 8b and 8c, of which the anodes are connected to the upper and lower plates respectively of the discharge capacitor 9. The upper plate of the capacitor 9 is connected to the anode of the thyristor 10a and the cathode of a thyristor 10d, the cathode of thyristor 10a and the anode thyristor 10d being connected to upper and lower terminals respectively of a stimulating coil 11. Similarly, the lower plate of the capacitor 9 is connected to the anode of thyristor 10b and to the cathode of thyristor 10c, the cathode of thyristor 10b and the anode of thyristor 10c being connected to the upper and lower terminals of the stimulating coil 11. The thyristors 10a to 10d constitute a bridge 10 which determines unidirectional flow of current through the coil 11 irrespective of the polarity of the voltage across the capacitor 5. In this embodiment the lower terminal of the stimulating coil 11 is provided with a ground connection 12.

As described in the aforementioned patent, the system described in FIG. 1 may be used for the repeated transfer of charge from the reservoir capacitor 2 to the transfer capacitor 5 and thence to the discharge capacitor 9 during appropriate time intervals. Modulation of the amplitude and frequency of the magnetic stimulating pulse fields provided by the coil 11 may be achieved.

The system shown in FIG. 1 may be multiplexed or combined with a plurality of other similar stimulating channels, as described in for example U.S. Pat. No. 5,718,662, so as to achieve a high pulse repetition rate.

As indicated previously, systems of this nature are subject to overheating of the coil 11 when rapid high power pulses are produced. Accordingly, the present invention provides for the cooling of the coil by means of a gaseous coolant.

Figure 2:
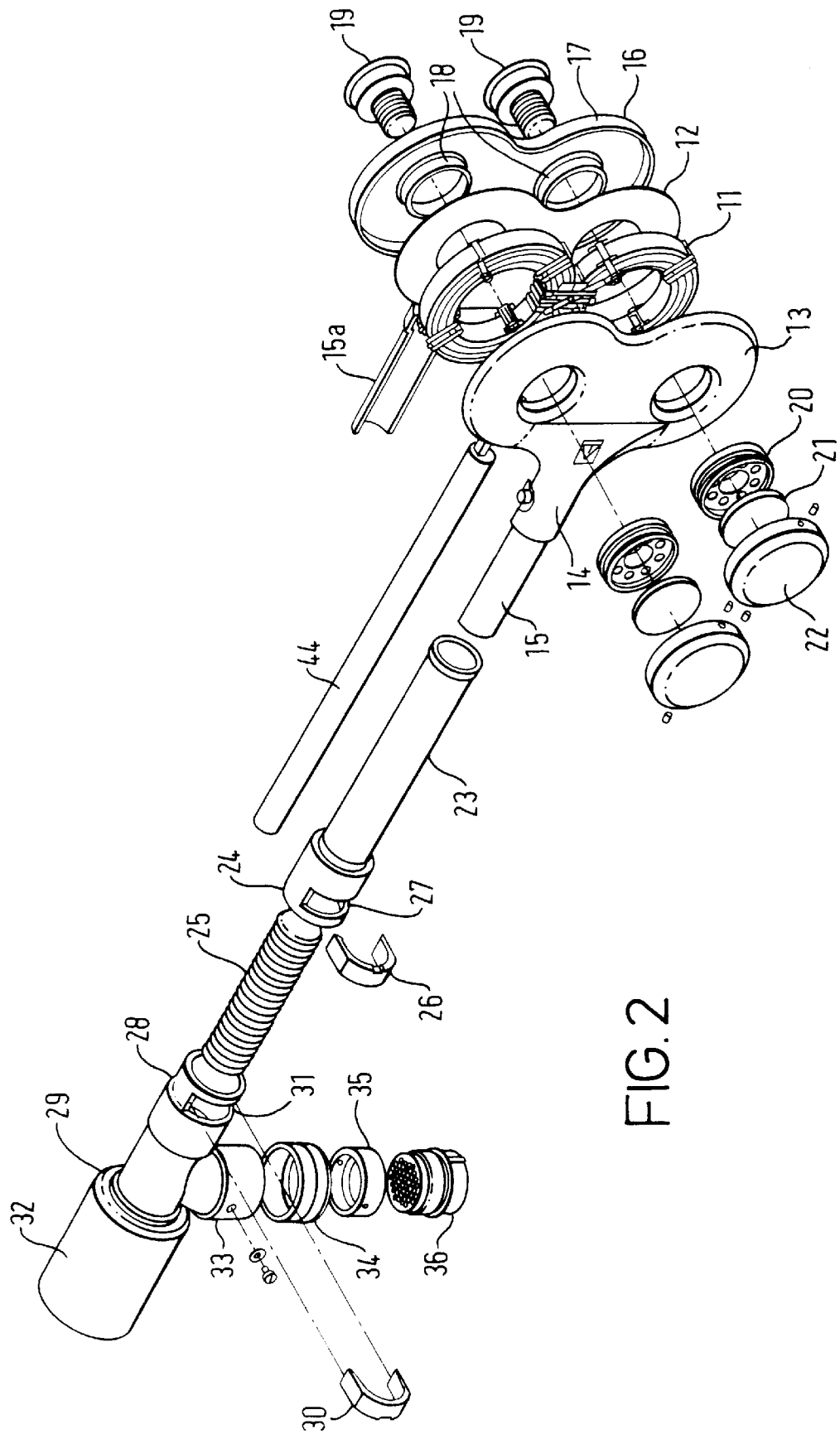
FIG. 2 is an 'exploded' view of a coil assembly according to the invention.
Figure 3:
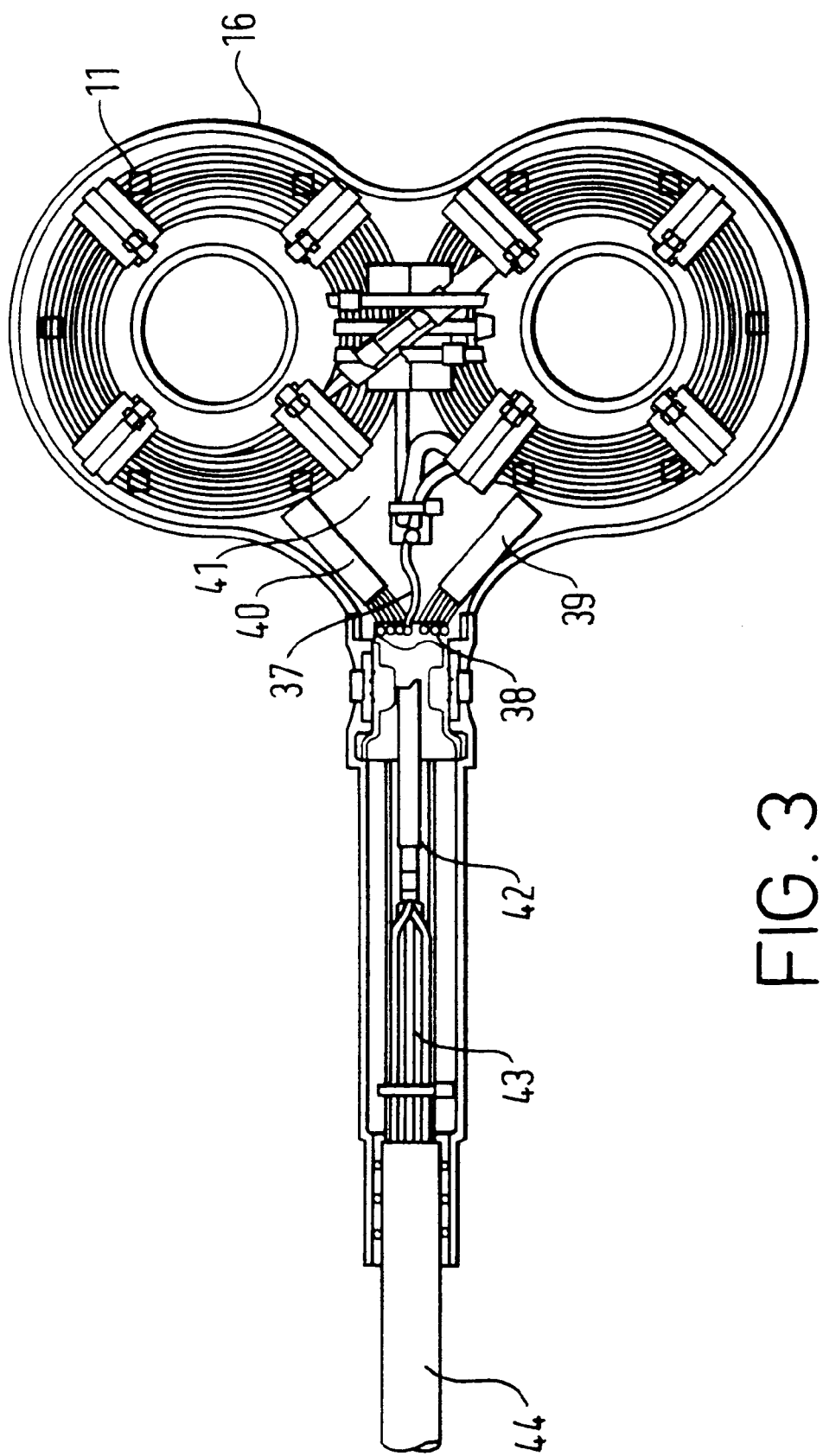
FIG. 3 is a sectional view of part of the assembly shown in FIG. 2.

FIGS. 2 and 3 illustrate one embodiment of an assembly for the coil allowing the coil to operate for relatively prolonged periods without overheating.

The description which follows is of a coil assembly which, broadly, has a casing in which the coil is disposed in a manner which allows the flow of coolant gas over the exposed surfaces of the coil. The assembly includes a hollow shaft which connects the casing for the coil to a further conduit and a T-piece having a branch for electrical cables that extends through the conduit and shaft to the coil and a branch for the flow of gas. In the preferred example, gas may be pumped by means of a vacuum suction pump through the assembly but an equivalent, which would require some modification to the embodiment, would be to allow for injection of compressed gas coolant into the assembly, for example at an inlet provided in the coil casing so that the gas exhausts at the other end of the conduit.

The assembly shown in the drawings includes the coil 11 which is disposed adjacent an insulating screen 12. The coil and screen are disposed within a casing comprising a top cover 13 in a generally figure of eight form having a side extension 14 terminating in a semi-circular pipe section 15. The bottom cover 16 is generally similar; it has a peripheral flange 17 and inner circular flanges 18 for the retention and location of the coil and the insulating screen 12. Through the holes in the figure of eight assembly extend two screws 19. These screws extend to filter assemblies comprising a respective filter well 20, a filter 21 fitting within the respective filter well, and a filter cap 22.

The semi-circular pipe sections 15 and 15a mutually abut and fit within a shaft 23 terminating in an adapter 24 for fitment over and securing to a nylon conduit 25. A clip 26 fits into a recess 27 in the adapter 24 in order to secure the conduit 25 in adapter 24. The other end of the conduit 25 fits into an adapter 28 of a T-piece assembly 29. A clip 30 fits into recess 31 to secure the conduit 25 in adapter 28. Branch 32 of T-piece 29 is intended for coupling to a vacuum suction pump (not shown). Depending from the body of the T-piece 31 is a short tube 33 to which is fitted a connector shell 34 within the lower end of which fits a ring spacer 35 within which fits a cable connector 36.

As is shown in FIG. 3, a ground wire 37 is connected to the insulating screen 12 and this screen is adhered into the bottom cover 16. A printed circuit board 38 is disposed in the bottom cover as are two heat sensors 39 and 40.

Cables 41 extend from the coil to the printed circuit board and the printed circuit board 38 is coupled by way of connectors 42 to a cable assembly 43 in a rigid tube 44 which extends along the inside of the shaft 23.

The cables are held rigidly as shown at 44 so that there is space for the passing of gaseous coolant through the assembly.

In the particular example shown in the drawings, air will be drawn in through the filters and after passing over the coil will be drawn out through the branch 32 of T-piece 29 after passing along the tube 23 and conduit 25.

Modifications are feasible. For example, compressed gas could be applied to an inlet in the casing and pass back along the cable conduit 25 to an exhaust at the T-piece.

Further modifications may be made by those skilled in the art, and it is intended only to illustrate and not limit the invention by the foregoing example.

What is claimed is:

1. A magnetic stimulator for neuro-muscular tissue, said stimulator comprising:

a stimulating coil and means for generating a succession of electrical discharge pulses of said coil to produce magnetic pulses for the inducement of electrical signals in the tissue, wherein the coil has at least one set of generally circular turns, and is disposed within a casing connected to a conduit through which extend cables for the supply of electrical power to the coil, and wherein the conduit and casing include an inlet and an outlet for a gaseous coolant and allow for the flow of gaseous coolant around and over exposed surfaces of the coil, through the casing and along the conduit.

2. A magnetic stimulator coil assembly as in claim 1 wherein:

said coil has the form of a figure of eight including two sets of generally circular turns, and the casing has a form of generally a figure of eight including a side extension, cables for the coil extending through the side extension.

3. A magnetic stimulator for neuro-muscular tissue, said stimulator comprising:

a stimulating coil and means for generating a succession of electrical discharge pulses in said coil to produce magnetic pulses for the inducement of electrical signals in the tissue, said coil being in the form of a figure of eight including two sets of generally circular turns;

a casing for said coil, said casing comprising a top cover in a generally figure of eight form having a side extension, a bottom cover similar to said top cover being in generally figure of eight form having a respective side extension, said top cover and bottom cover defining holes encircled by the respective set of turns; and filter assemblies each disposed in a respective one of said holes, said filter assemblies each allowing air to pass into the housing and over the coil.

4. A magnetic stimulator for neuro-muscular tissue, said stimulator comprising:

an elongated tubular member having proximal and distal ends;

at least one electromagnetic coil disposed in a housing at the distal end of said tubular member and in fluid communication with the tubular member;

electrical current supply conductors connected to said coil and extending therefrom within said tubular member towards its proximal end;

at least one gaseous cooling fluid inlet disposed in said housing proximate said coil; and a gaseous cooling fluid outlet disposed towards the proximal end of said tubular member;

whereby gaseous cooling fluid may be caused to flow about said coil and supply conductors within and through said housing and tubular member.

5. A magnetic stimulator as in claim 4 further comprising:

a gaseous cooling fluid filter disposed in said at least one inlet of the housing.

6. A magnetic stimulator as in claim 4 wherein:

the coil comprises adjacent circular sections of coil windings around in a figure eight configuration; and the housing has at least one gaseous cooling fluid inlet disposed within the center of each said circular section.

7. A magnetic stimulator as in claim 5 further comprising a gaseous cooling fluid filter disposed in each inlet of the housing.

8. A magnetic stimulator as in claim 4 wherein said electrical conductors are connected to a fluid tight electrical connector disposed along said tubular member before the proximal end and fluid outlet of the tubular member.

9. A magnetic stimulator as in claim 4 wherein said housing is formed of two split housing half-sections held together with fasteners engaging the at least one fluid inlet of the housing.

* * * * *